United States Patent
Augier et al.

(10) Patent No.: US 12,157,712 B2
(45) Date of Patent: Dec. 3, 2024

(54) OLIGOMERIZATION PROCESS IMPLEMENTING THE RECYCLING OF THE GAS HEADSPACE

(71) Applicant: IFP Energies nouvelles, Rueil-Malmaison (FR)

(72) Inventors: Frederic Augier, Rueil-Malmaison (FR); Alexandre Vonner, Rueil-Malmaison (FR); Pedro Maximiano Raimundo, Rueil-Malmaison (FR); Lionel Magna, Rueil-Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 110 days.

(21) Appl. No.: 18/017,184

(22) PCT Filed: Jul. 13, 2021

(86) PCT No.: PCT/EP2021/069449
§ 371 (c)(1),
(2) Date: Jan. 20, 2023

(87) PCT Pub. No.: WO2022/017869
PCT Pub. Date: Jan. 27, 2022

(65) Prior Publication Data
US 2023/0286884 A1 Sep. 14, 2023

(30) Foreign Application Priority Data
Jul. 24, 2020 (FR) ...................................... 2007845

(51) Int. Cl.
*C07C 2/24* (2006.01)
*B01J 10/00* (2006.01)
(Continued)

(52) U.S. Cl.
CPC ................. *C07C 2/24* (2013.01); *B01J 10/00* (2013.01); *B01J 19/0013* (2013.01);
(Continued)

(58) Field of Classification Search
CPC ......... C07C 2/24; C07C 2523/26; C07C 2/08; C07C 2/32; B01J 10/00; B01J 19/0013;
(Continued)

(56) References Cited

U.S. PATENT DOCUMENTS

| 10,399,912 B2 * | 9/2019 | Han ........................... C08F 6/10 |
| 2009/0203947 A1 * | 8/2009 | Schneider ................. C07C 7/09 422/198 |

(Continued)

FOREIGN PATENT DOCUMENTS

| WO | 2016009360 A1 | 1/2016 |
| WO | 2019011806 A1 | 1/2019 |

OTHER PUBLICATIONS

International Search Report for PCT/EP2021/069449 dated Oct. 7, 2021.

*Primary Examiner* — Ali Z Fadhel
(74) *Attorney, Agent, or Firm* — MILLEN, WHITE, ZELANO & BRANIGAN, P.C.; Brion P. Heaney

(57) ABSTRACT

The present invention relates to an oligomerization process implemented in a sequence of at least two gas/liquid reactors, placed in series, comprising at least one gas headspace recycle loop. The process more particularly relates to the oligomerization of ethylene to linear alpha-olefins such as 1-butene, 1-hexene, 1-octene or a mixture of linear alpha-olefins.

17 Claims, 1 Drawing Sheet

(51) Int. Cl.
*B01J 19/00* (2006.01)
*B01J 19/24* (2006.01)

(52) U.S. Cl.
CPC ......... *B01J 19/245* (2013.01); *B01J 19/2465* (2013.01); *B01J 2219/00033* (2013.01); *B01J 2219/0011* (2013.01); *C07C 2523/26* (2013.01)

(58) Field of Classification Search
CPC .................. B01J 19/245; B01J 19/2465; B01J 2219/00033; B01J 2219/0011; B01J 2219/00087; B01J 10/002; B01J 4/004
See application file for complete search history.

(56) References Cited

U.S. PATENT DOCUMENTS

| | | | |
|---|---|---|---|
| 2010/0249343 A1* | 9/2010 | Kleingeld | C07C 2/36 526/348 |
| 2012/0330078 A1* | 12/2012 | Hofmann | C07C 2/08 585/520 |
| 2015/0126790 A1* | 5/2015 | Venter | C07C 2/32 585/511 |
| 2015/0291486 A1* | 10/2015 | Weber | C08F 2/42 585/512 |
| 2015/0299069 A1 | 10/2015 | Azam et al. | |
| 2017/0210680 A1 | 7/2017 | Azam et al. | |
| 2020/0139334 A1* | 5/2020 | Al-Dughaiter | C07C 2/08 |
| 2020/0199039 A1 | 6/2020 | Azam et al. | |
| 2021/0009486 A1* | 1/2021 | Allen | C07C 2/08 |
| 2021/0077977 A1 | 3/2021 | Augier et al. | |

* cited by examiner

OLIGOMERIZATION PROCESS IMPLEMENTING THE RECYCLING OF THE GAS HEADSPACE

TECHNICAL FIELD

The present invention relates to an oligomerization process implemented in a sequence of at least two gas/liquid reactors, placed in series, comprising at least one gas headspace recycle loop. The process more particularly relates to the oligomerization of ethylene to linear alpha-olefins such as 1-butene, 1-hexene, 1-octene or a mixture of linear alpha-olefins.

PRIOR ART

The invention relates to the field of oligomerization processes employing gas/liquid reactors, which are also called bubble columns. Owing to the exothermic nature of oligomerization reactions, bubble columns likewise comprise a recirculation loop whereby a liquid fraction is withdrawn, cooled and reintroduced into the reaction chamber. Said recirculation loop makes it possible to obtain good homogeneity of the concentrations and to control the temperature throughout the reaction volume, due to the good heat transfer capacity related to the recirculation loop.

One disadvantage encountered in oligomerization processes when using this type of column is the management of the gas phase, also known as the gas headspace. The reason is that said gas headspace comprises gaseous components of low solubility in the liquid phase, compounds which are partially soluble in the liquid but are inert, and gaseous ethylene not dissolved in said liquid. The passage of gaseous ethylene from the liquid phase toward the gas phase (or gas headspace) is a phenomenon referred to as breakthrough. In point of fact, the gas headspace is bled in order to remove said gaseous compounds. When the amount of gaseous ethylene present in the gas headspace is high, the bleeding of the gas headspace leads to a not insignificant loss of ethylene, which is detrimental to the productivity and to the cost of the oligomerization process.

To improve the efficiency of the oligomerization process, in particular in terms of productivity and cost, it is therefore vital to limit the loss of unreacted ethylene contained in the gas headspace so as to improve its conversion in said process, while retaining a high selectivity for desired linear alpha-olefins.

The prior art processes employing a liquid recirculation loop, as illustrated in FIG. 1, do not make it possible to limit the loss of gaseous ethylene, and the purging of the gas headspace results in an exit of gaseous ethylene from the reactor that is adverse for the yield and the cost of the process.

The applicant has described, in applications WO2019/011806 and WO2019/011609, processes which make it possible to increase the contact surface area between the upper part of the liquid fraction and the gas headspace via dispersion or vortex means, in order to promote the passage of the ethylene contained in the gas headspace to the liquid phase at the liquid/gas interface. These processes may, however, be insufficient when the amount of ethylene in the gas headspace is substantial because of a high degree of breakthrough.

Moreover, during its research studies, the applicant has found that, in a reactor operating with a constant flow rate of injected gaseous ethylene, the amount of dissolved ethylene and thus the degree of breakthrough are dependent on the dimensions of the reactors implementing the process and notably on the height of the liquid phase. This is because the lower the height, the shorter the time during which the gaseous ethylene travels through the liquid phase to dissolve and the higher the degree of breakthrough.

Surprisingly, the applicant has discovered a new process using a sequence of at least two gas/liquid reactors placed in series and comprising at least one step of recycling at least one fraction of the gas headspace into the lower part of the liquid phase in the first reactor of the series, making it possible to optimize the dissolution of the gaseous ethylene involved in the process, and to adjust the pressure within the first reactor without leading to a loss of ethylene. In particular, the process makes it possible to obtain selective production of linear alpha-olefins such as 1-butene, 1-hexene or 1-octene.

Another advantage of the process according to the invention is that it makes it possible to achieve higher levels of selectivity and of conversion, and also to limit the cost of implementing it, using a sequence of gas/liquid reactors according to the invention.

Another advantage of the recycling step according to the invention is that it enables simple and economic compensation of the phenomenon of breakthrough of the gaseous ethylene into the gas headspace in an oligomerization process, irrespective of the dimensions of the reactor.

BRIEF DESCRIPTION OF THE INVENTION

A subject of the present invention relates to a process for the oligomerization of ethylene, carried out at a pressure of between 0.1 and 10 MPa, at a temperature of between 30 and 200° C., in a sequence of at least two gas/liquid reactors placed in series, said process comprising the following steps:

a) a step of introducing a catalytic oligomerization system comprising at least one metal precursor, optionally at least one activating agent and optionally at least one additive into at least the first reactor of the sequence comprising a reaction chamber comprising a liquid phase in a lower zone and a gas phase in an upper zone, b) a step of introducing gaseous ethylene into the lower part of the reaction chamber of at least the first reactor of the sequence, c) for each reactor, a step of withdrawing a fraction of liquid phase from the lower part of the reaction chamber of the reactor, the liquid fraction being separated into two streams: a first stream corresponding to a first portion of the liquid fraction, termed main liquid fraction, which is sent to the cooling step e); a second stream corresponding to the second portion of the liquid fraction which constitutes the liquid feed of the reactor, located downstream in the sequence, unless the liquid fraction withdrawn is from the final reactor of the sequence, and for the final reactor of the sequence, the second stream corresponds to the effluent obtained at the end of the oligomerization process, d) a step of introducing said second portion of the liquid fraction withdrawn from the reactor located upstream into the reaction chamber of the reactor located downstream in the direction of flow, e) a step of cooling said main liquid fraction withdrawn from the reactor located upstream in step c) by passing said first portion of the liquid fraction into a heat exchanger in order to obtain a cooled liquid fraction, f) a step of introducing said liquid fraction cooled in step e) at the top of the reaction chamber of said reactor, steps a) to f) being carried out for each reactor of the sequence, g) a step of recycling a gas fraction, withdrawn from the upper zone of the reaction chamber and introduced at the lower part of said reaction chamber into the liquid phase, said recycling step g) being carried out in at least the first reactor of the sequence.

Preferably, the sequence of reactors uses from 2 to 10 gas/liquid reactors placed in series.

Preferably, the gas phase withdrawn in step g) is introduced as a mixture with the gaseous ethylene introduced in step b).

Preferably, the rate of withdrawal of the gas fraction in step g) is between 0.1 and 100% of the flow rate of gaseous ethylene introduced in step b).

Preferably, the gas fraction withdrawn in step g) is introduced at the lateral lower part of the reaction chamber.

Preferably, the rate of withdrawal of the gas fraction in step g) is controlled by the pressure within the reaction chamber.

Preferably, a second purge gas stream is withdrawn from the gas phase. Preferably, the flow rate of the second gaseous stream is between 0.005 and 1.00% of the flow rate of ethylene introduced in step b).

Preferably, the process also uses a solvent and has a content by weight of solvent introduced into the sequence of reactors of between 0.5 and 10.0.

Preferably, a gaseous hydrogen stream is introduced in step b) into the reaction chamber, with a flow rate representing 0.2 to 5.0% by weight of the flow rate of incoming ethylene.

Preferably, the concentration of metal precursor in the catalytic system is between 0.1 and 50.0 ppm by weight of atomic metal relative to the reaction mass.

Preferably, the catalytic oligomerization reaction is carried out continuously.

Preferably, the oligomerization makes it possible to obtain linear olefins comprising from 4 to 20 carbon atoms.

Another subject of the invention relates to a reaction device for implementing the process described above, wherein each of the reactors comprises the following elements:

- a reaction chamber i), of elongate shape along the vertical axis, a lower zone and an upper zone above the lower zone,
- an optional means ii) for introducing gaseous ethylene into said reaction chamber, the first reactor of the sequence always comprising said means ii) for introducing the gaseous ethylene,
- an optional means iii) for introducing the catalytic system, the first reactor of the sequence always comprising said means iii) for introducing the catalytic system,
- a recirculation loop iv) comprising a withdrawing means at the base of the reaction chamber for withdrawing a liquid fraction and a heat exchanger, and a means for introducing said cooled liquid into the upper part of the lower zone of the reaction chamber,
- a gas phase recycle loop v), comprising a means for withdrawing a gas fraction at the level of the upper zone of the reaction chamber, and a means for introducing said withdrawn gas fraction into the lower zone of the reaction chamber,
- with the exception of the first reactor, at least one means vi) for feeding a second portion of the liquid fraction withdrawn from the upstream reactor in the sequence, said one or more feed means vi) preferably being a pipe directly feeding the reaction chamber, or a pipe joining the recirculation loop used for the cooling step e), at least the first reactor of the sequence always being fed with catalytic system and with gaseous ethylene.

Preferably, the introduction of the withdrawn gas fraction into the recycle loop is carried out via the means ii) for introducing the gaseous ethylene.

DEFINITIONS & ABBREVIATIONS

Throughout the description, the terms or abbreviations below have the following meanings.

Oligomerization is understood to mean any addition reaction of a first olefin with a second olefin identical to or different from the first olefin. The olefin thus obtained has the empirical formula $C_nH_{2n}$, where n is equal to or greater than 4.

Alpha-olefin is understood to mean an olefin wherein the double bond is located at the terminal position of the alkyl chain.

Catalytic system is understood to mean the mixture of at least one metal precursor and of at least one activating agent, in the presence optionally of at least one additive and optionally in the presence of at least one solvent.

Liquid phase is understood to mean the mixture of all of the compounds which are in a liquid physical state under the temperature and pressure conditions of the reaction chamber.

The term "gas phase", also referred to as headspace, is understood to mean the mixture of all of the compounds which are in the gaseous physical state under the temperature and pressure conditions of the reaction chamber: in the form of bubbles present in the liquid, and also in the top part of the reaction chamber (headspace of the reactor).

The term "lower zone" of the reaction chamber is understood to mean the part of the chamber that comprises the liquid phase, gaseous ethylene, products of the reaction such as the desired linear alpha-olefin (i.e. 1-butene, 1-hexene, 1-octene), and the catalytic system.

The term "upper zone" of the reaction chamber is understood to mean the part of the reaction chamber that is located at the top of the reaction chamber, in other words directly above the lower zone and consisting of the gas headspace.

The expression "lateral lower part of the reaction chamber" is understood to mean a part of the shell of the reactor located in the bottom part and on the side.

The term "noncondensable gas" is understood to mean an entity in gaseous physical form which only partially dissolves in the liquid at the temperature and pressure conditions of the reaction chamber and which can, under certain conditions, accumulate in the headspace of the reactor (example here: ethane).

The term "t/h" is understood to mean the value of a flow rate expressed in tonnes per hour and the term "kg/s" is understood to mean the value of a flow rate in kilograms per second.

The terms "reactor" or "device" denote all of the means which make possible the implementation of the oligomerization process according to the invention, such as notably the reaction chamber and the recirculation loop.

The term "lower part of the lower zone of the reaction chamber" is understood to mean the lower quarter of the reaction chamber containing the liquid phase.

The term "upper part of the lower zone of the reaction chamber" is understood to mean the upper quarter of the reaction chamber containing the liquid phase.

The term "fresh gaseous ethylene" is understood to mean the ethylene external to the process that is introduced in step b) via the means ii) of the process according to the invention.

The terms "upstream" and "downstream" should be understood as a function of the general flow of the stream in the sequence of reactors, from the introduction of the reagents, such as ethylene in this case, up to the recovery of the product of interest, namely the α-olefin(s) under consideration in the process.

The term "content by weight of solvent" is understood to mean the ratio by weight of the total flow rate of solvent injected to the total flow rate of fresh gaseous ethylene entering the reactors used in the process.

The term "reaction mass" is understood to mean the total weight of a liquid phase of a given reactor comprising all the entities in the liquid or dissolved state in said liquid phase.

DETAILED DESCRIPTION OF THE INVENTION

It is specified that, throughout this description, the expression "between . . . and . . . " should be understood as including the limits mentioned.

For the purposes of the present invention, the various embodiments presented may be used alone or in combination with one another, without any limit to the combinations.

For the purposes of the present invention, the various ranges of parameters for a given step, such as the pressure ranges and the temperature ranges, may be used alone or in combination. For example, for the purposes of the present invention, a preferred range of pressure values can be combined with a more preferred range of temperature values.

The present invention relates to a process for the oligomerization of ethylene, carried out at a pressure of between 0.1 and 10 MPa, at a temperature of between 30 and 200° C., in a sequence of at least two gas/liquid reactors placed in series, said process comprising the following steps:
   a) a step of introducing a catalytic oligomerization system comprising at least one metal precursor, optionally at least one activating agent and optionally at least one additive into at least the first reactor of the sequence comprising a reaction chamber comprising a liquid phase in a lower zone and a gas phase in an upper zone,
   b) a step of introducing gaseous ethylene into the lower part of the reaction chamber of at least the first reactor of the sequence,
   c) for each reactor, a step of withdrawing a fraction of liquid phase from the lower part of the reaction chamber of the reactor, the liquid fraction being separated into two streams: a first stream corresponding to a first portion of the liquid fraction, termed main liquid fraction, which is sent to the cooling step e); a second stream corresponding to the second portion of the liquid fraction which constitutes the liquid feed of the reactor, located downstream in the sequence, unless the liquid fraction withdrawn is from the final reactor of the sequence, and for the final reactor of the sequence, the second stream corresponds to the effluent obtained at the end of the oligomerization process,
   d) a step of introducing said second portion of the liquid fraction withdrawn from the reactor located upstream into the reaction chamber of the reactor located downstream in the direction of flow,
   e) a step of cooling said main liquid fraction withdrawn from the reactor located upstream in step c) by passing said first portion of the liquid fraction into a heat exchanger in order to obtain a cooled liquid fraction,
   f) a step of introducing said liquid fraction cooled in step e) at the top of the reaction chamber of said reactor, steps a) to f) being carried out for each reactor of the sequence,
   g) a step of recycling a gas fraction, withdrawn from the upper zone of the reaction chamber and introduced at the lower part of said reaction chamber into the liquid phase, said recycling step g) being carried out in at least the first reactor of the sequence.

Preferably, in a gas/liquid reactor, the flow rate of gaseous ethylene introduced in step b) is controlled by the pressure in the reaction chamber, so as to maintain the pressure, advantageously between 0.1 and 10 MPa, in the reaction chamber. In the event of an increase in the pressure in the reactor, therefore, owing to a high degree of breakthrough by the ethylene into the gas phase, the flow rate of gaseous ethylene introduced in step b) goes down, leading to a decrease in the amount of ethylene dissolved in the liquid phase, and hence in the ethylene saturation. Said decrease is prejudicial for the productivity of the process, and also for the selectivity thereof.

The process according to the invention advantageously has a degree of saturation of dissolved ethylene in the liquid phase of more than 70.0%, preferably between 70.0 and 100%, preferably between 80.0 and 100%, preferentially between 80.0 and 99.0%, preferably between 85.0 and 99.0% and even more preferably between 90.0 and 98.0%.

The degree of saturation of dissolved ethylene can be measured by any method known to those skilled in the art and, for example, by gas chromatography (commonly referred to as GC) analysis of a fraction of the liquid phase withdrawn from the reaction chamber.

Another advantage of the step of recycling at least one fraction of the gas headspace according to the invention is that it enables simple and economic compensation of the phenomenon of breakthrough of the gaseous ethylene into the gas headspace in an oligomerization process, irrespective of the dimensions of the reactor.

Another advantage of the present invention is that it improves the ethylene conversion of ethylene and/or the selectivity for olefins, and also the volumetric productivity of the oligomerization process.

Oligomerization Process

The ethylene oligomerization process according to the invention makes it possible to produce linear α-olefins by placing in contact ethylene and a catalytic system, optionally in the presence of a solvent.

All catalytic systems known to those skilled in the art and capable of being employed in the dimerization, trimerization or tetramerization processes and more generally in the oligomerization processes according to the invention come within the field of the invention. Said catalytic systems and also the uses thereof are described notably in applications FR 2 984 311, FR 2 552 079, FR 3 019 064, FR 3 023 183, FR 3 042 989 or else in application FR 3 045 414.

Preferably, the catalytic systems comprise, preferably consist of:
   a metal precursor, preferably based on nickel, on titanium or on chromium,
   optionally an activating agent,
   optionally an additive, and
   optionally a solvent.

The Metal Precursor

The metal precursor used in the catalytic system is preferably chosen from compounds based on nickel, on titanium or on chromium.

In one embodiment, the metal precursor is based on nickel and preferentially comprises nickel of (+II) oxidation state. Preferably, the nickel precursor is chosen from nickel(II) carboxylates, such as, for example, nickel 2-ethylhexanoate, nickel(II) phenates, nickel(II) naphthenates, nickel(II) acetate, nickel(II) trifluoroacetate, nickel(II) triflate, nickel (II) acetylacetonate, nickel(II) hexafluoroacetylacetonate, π-allylnickel(II) chloride, π-allylnickel(II) bromide, methallylnickel(II) chloride dimer, $\eta^3$-allylnickel(II) hexafluorophosphate, $\eta^3$-methallylnickel(II) hexafluorophosphate and nickel(II) 1,5-cyclooctadienyl, in their hydrated or non-hydrated form, taken alone or as a mixture.

In a second embodiment, the metal precursor is based on titanium and preferentially comprises a titanium aryloxy or alkoxy compound.

The titanium alkoxy compound advantageously corresponds to the general formula [Ti(OR)$_4$] wherein R is a linear or branched alkyl radical. Mention may be made, among the preferred alkoxy radicals, as non-limiting examples, of tetraethoxy, tetraisopropoxy, tetra(n-butoxy) and tetra(2-ethylhexyloxy).

The titanium aryloxy compound advantageously corresponds to the general formula [Ti(OR')$_4$] wherein R' is an aryl radical substituted or unsubstituted with alkyl or aryl groups. The radical R' can comprise heteroatom-based substituents. The preferred aryloxy radicals are chosen from phenoxy, 2-methylphenoxy, 2,6-dimethylphenoxy, 2,4,6-trimethylphenoxy, 4-methylphenoxy, 2-phenylphenoxy, 2,6-diphenylphenoxy, 2,4,6-triphenylphenoxy, 4-phenylphenoxy, 2-(tert-butyl)-6-phenylphenoxy, 2,4-di(tert-butyl)-6-phenylphenoxy, 2,6-diisopropylphenoxy, 2,6-di(tert-butyl) phenoxy, 4-methyl-2,6-di(tert-butyl)phenoxy, 2,6-dichloro-4-(tert-butyl)phenoxy and 2,6-dibromo-4-(tert-butyl) phenoxy, the biphenoxy radical, binaphthoxy or 1,8-naphthalenedioxy.

According to a third embodiment, the metal precursor is based on chromium and preferentially comprises a chromium(II) salt, a chromium(III) salt or a salt of different oxidation state which can comprise one or more identical or different anions, such as, for example, halides, carboxylates, acetylacetonates or alkoxy or aryloxy anions. Preferably, the chromium-based precursor is chosen from CrCl$_3$, CrCl$_3$(tetrahydrofuran)$_3$, Cr(acetylacetonate)$_3$, Cr(naphthenate)$_3$, Cr(2-ethylhexanoate)$_3$ and Cr(acetate)$_3$.

The concentration of nickel, of titanium or of chromium is between 0.001 and 300.0 ppm by weight of atomic metal, relative to the reaction mass, preferably between 0.002 and 100.0 ppm, preferentially between 0.003 and 50.0 ppm, more preferentially between 0.05 and 20.0 ppm and even more preferentially between 0.1 and 10.0 ppm by weight of atomic metal, relative to the reaction mass.

The Activating Agent

Optionally, whatever the metal precursor, the catalytic system can comprise one or more activating agents preferably chosen from aluminum-based compounds, such as methylaluminum dichloride (MeAlCl$_2$), dichloroethylaluminum (EtAlCl$_2$), ethylaluminum sesquichloride (Et$_3$Al$_2$Cl$_3$), chlorodiethylaluminum (Et$_2$AlCl), chlorodiisobutylaluminum (i-Bu$_2$AlCl), triethylaluminum (AlEt$_3$), tripropylaluminum (Al(n-Pr)$_3$), triisobutylaluminum (Al(i-Bu)$_3$), diethylethoxyaluminum (Et$_2$AlOEt), methylaluminoxane (MAO), ethylaluminoxane and modified methylaluminoxanes (MMAO).

The Additive

Optionally, the catalytic system can comprise one or more additives.

The additive is preferably chosen from monodentate phosphorus-containing compounds, bidentate phosphorus-containing compounds, tridentate phosphorus-containing compounds, olefinic compounds, aromatic compounds, nitrogenous compounds, bipyridines, diimines, monodentate ethers, bidentate ethers, monodentate thioethers, bidentate thioethers, monodentate or bidentate carbenes, mixed ligands such as phosphinopyridines, iminopyridines, bis (imino)pyridines.

When the catalytic system is based on nickel, the additive is advantageously chosen from:
  compounds of nitrogenous type, such as trimethylamine, triethylamine, pyrrole, 2,5-dimethylpyrrole, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluoromethylpyridine, 2-phenylpyridine, 3-phenylpyridine, 2-benzylpyridine, 3,5-dimethylpyridine, 2,6-di(tert-butyl)pyridine and 2,6-diphenylpyridine, quinoline, 1,10-phenanthroline, N-methylpyrrole, N-butylpyrrole, N-methylimidazole, N-butylimidazole, 2,2'-bipyridine, N,N'-dimethylethane-1,2-diimine, N,N'-di(t-butyl)ethane-1,2-diimine, N,N'-di(t-butyl)butane-2,3-diimine, N,N'-diphenylethane-1,2-diimine, N,N'-bis(2,6-dimethylphenyl)ethane-1,2-diimine, N,N'-bis(2,6-diisopropylphenyl)ethane-1,2-diimine, N,N'-diphenylbutane-2,3-diimine, N,N'-bis(2,6-dimethylphenyl)butane-2,3-diimine or N,N'-bis(2,6-diisopropylphenyl)butane-2,3-diimine, or
  compounds of phosphine type independently chosen from tributylphosphine, triisopropylphosphine, tricyclopentylphosphine, tricyclohexylphosphine, triphenylphosphine, tris(o-tolyl)phosphine, bis(diphenylphosphino) ethane, trioctylphosphine oxide, triphenylphosphine oxide or triphenyl phosphite, or
  compounds corresponding to the general formula (I) or one of the tautomers of said compound:

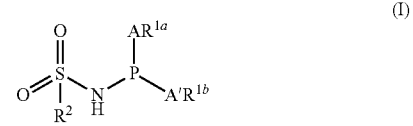

wherein:
  A and A', which may be identical or different, are independently an oxygen or a single bond between the phosphorus atom and a carbon atom,
  the $R^{1a}$ and $R^{1b}$ groups are independently chosen from the methyl, trifluoromethyl, ethyl, n-propyl, isopropyl, n-butyl, isobutyl, t-butyl, pentyl, cyclohexyl or adamantyl groups, which are substituted or unsubstituted and contain or do not contain heteroelements; the phenyl, o-tolyl, m-tolyl, p-tolyl, mesityl, 3,5-dimethylphenyl, 4-(n-butyl)phenyl, 2-methylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di(tert-butyl)-4-methoxyphenyl, 4-chlorophenyl, 3,5-di(trifluoromethyl)phenyl, benzyl, naphthyl, bisnaphthyl, pyridyl, bisphenyl, furanyl or thiophenyl groups, the R² group is independently chosen from the methyl, trifluoromethyl, ethyl, n-propyl, isopropyl, n-butyl, isobutyl, t-butyl, pentyl, cyclohexyl or adamantyl groups, which are substituted or unsubstituted and contain or do not contain heteroelements; the phenyl, o-tolyl, m-tolyl, p-tolyl, mesityl, 3,5-dimethylphenyl, 4-(n-butyl)phenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di(tert-butyl)-4-methoxyphenyl, 4-chlorophenyl, 3,5-bis(trifluoromethyl)phenyl, benzyl, naphthyl, bisnaphthyl, pyridyl, bisphenyl, furanyl or thiophenyl groups.

When the catalytic system is based on titanium, the additive is chosen from diethyl ether, diisopropyl ether, dibutyl ether, diphenyl ether, 2-methoxy-2-methylpropane, 2-methoxy-2-methylbutane, 2,2-dimethoxypropane, 2,2-bis(2-ethylhexyloxy)propane, 2,5-dihydrofuran, tetrahydrofuran, 2-methoxytetrahydrofuran, 2-methyltetrahydrofuran, 3-methyltetrahydrofuran, 2,3-dihydropyran, tetrahydropyran, 1,3-dioxolane, 1,3-dioxane, 1,4-dioxane, dimethoxyethane, bis(2-methoxyethyl) ether, benzofuran, glyme and diglyme, taken alone or as a mixture.

When the catalytic system is based on chromium, the additive is advantageously chosen from:
  compounds of nitrogenous type, such as trimethylamine, triethylamine, pyrrole, 2,5-dimethylpyrrole, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluoromethylpyridine, 2-phenylpyridine, 3-phenylpyridine, 2-benzylpyridine, 3,5-dimethylpyridine, 2,6-di(tert-butyl)pyridine and 2,6-diphenylpyridine, quinoline, 1,10-phenanthroline, N-methylpyrrole, N-butylpyrrole, N-methylimidazole, N-butylimidazole, 2,2'-bipyridine, N,N'-dimethylethane-1,2-diimine, N,N'-di(t-butyl)ethane-1,2-diimine, N,N'-di(t-butyl)butane-2,3-diimine, N,N'-diphenylethane-1,2-diimine, N,N'-bis(2,6-dimethylphenyl)ethane-1,2-diimine, N,N'-bis(2,6-diisopropylphenyl)ethane-1,2-diimine, N,N'-diphenylbutane-2,3-diimine, N,N'-bis(2,6-dimethylphenyl)butane-2,3-diimine or N,N'-bis(2,6-diisopropylphenyl)butane-2,3-diimine, or aryloxy compounds of general formula $[M(R^3O)_{2-n}X_n]_y$, wherein:
  M is chosen from magnesium, calcium, strontium and barium, preferably magnesium,
  $R^3$ is an aryl radical containing from 6 to 30 carbon atoms and X is a halogen or an alkyl radical containing from 1 to 20 carbon atoms,
  n is an integer which can take the values of 0 or 1, and
  y is an integer between 1 and 10; preferably, y is equal to 1, 2, 3 or 4.

Preferably, the aryloxy radical $R^3O$ is chosen from 4-phenylphenoxy, 2-phenylphenoxy, 2,6-diphenylphenoxy, 2,4,6-triphenylphenoxy, 2,3,5,6-tetraphenylphenoxy, 2-(tert-butyl)-6-phenylphenoxy, 2,4-di(tert-butyl)-6-phenylphenoxy, 2,6-diisopropylphenoxy, 2,6-dimethylphenoxy, 2,6-di(tert-butyl)phenoxy, 4-methyl-2,6-di(tert-butyl)phenoxy, 2,6-dichloro-4-(tert-butyl)phenoxy and 2,6-dibromo-4-(tert-butyl)phenoxy. The two aryloxy radicals can be carried by one and the same molecule, such as, for example, the biphenoxy radical, binaphthoxy or 1,8-naphthalenedioxy. Preferably, the aryloxy radical $R^3O$ is 2,6-diphenylphenoxy, 2-(tert-butyl)-6-phenylphenoxy or 2,4-di(tert-butyl)-6-phenylphenoxy, heteroatomic compounds of general formula (I)

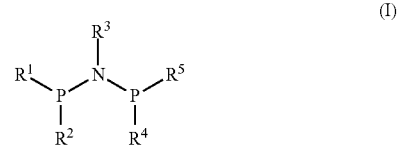

wherein:
  $R^1$, $R^2$, $R^3$, $R^4$ and $R^5$ which may be identical to or different than one another, optionally bonded to one another, are chosen from a cyclic or noncyclic, aromatic or nonaromatic alkyl group having from 1 to 15 carbon atoms, optionally containing heteroelements.

Preferably, the $R^1$, $R^2$, $R^3$, $R^4$ and $R^5$ groups, which may be identical to or different than one another, optionally bonded to one another, are chosen from the methyl, ethyl, n-propyl, isopropyl, n-butyl, isobutyl, ter-butyl, pentyl, cyclopentyl, hexyl, cyclohexyl or adamantyl groups, which are substituted or unsubstituted, and which optionally contain heteroelements; the phenyl, o-tolyl, m-tolyl, p-tolyl, mesityl, 3,5-dimethylphenyl, 4-n-butylphenyl, 2-methoxyphenyl, 3-methoxyphenyl, 4-methoxyphenyl, 2-isopropylphenyl, 4-methoxy-3,5-dimethylphenyl, 3,5-di-tert-butyl-4-methoxyphenyl, 2-chlorophenyl, 3-chlorophenyl, 4-chlorophenyl, 2-fluorophenyl, 3-fluorophenyl, 4-fluorophenyl, 4-trifluoromethylphenyl, 3,5-di(trifluoromethyl)phenyl, benzyl, naphthyl, bisnaphthyl, pyridyl, furanyl or thiophenyl groups, which are substituted or unsubstituted.

By way of nonlimiting example, mention may be made of the following heteroatomic compounds: (phenyl)₂PN(methyl)P(phenyl)₂, (phenyl)₂PN(i-propyl)P(phenyl)₂, (phenyl)₂PN(phenyl)P(phenyl)₂, (2-methoxyphenyl)₂PN(i-propyl)P(phenyl)₂, (2-methoxyphenyl)₂PN(i-propyl)P(2-methoxyphenyl)₂, (4-methoxyphenyl)₂PN(i-propyl) P(4-methoxyphenyl)₂, (2-fluorophenyl)₂PN(i-propyl)P(2-fluorophenyl)₂, (2-fluorophenyl)(phenyl)PN(i-propyl)P(2-fluorophenyl)₂, (2-fluorophenyl)(phenyl)PN(i-propyl)P(2-fluorophenyl)(phenyl), (2-fluorophenyl)(phenyl)PN(i-propyl)P(phenyl)₂.

The Solvent

In one embodiment according to the invention, the catalytic system optionally comprises one or more solvents.

In one embodiment, a solvent or a mixture of solvents can be used in the ethylene oligomerization process.

The solvent(s) are advantageously chosen from ethers, alcohols, halogenated solvents and hydrocarbons, which are saturated or unsaturated, cyclic or non-cyclic, aromatic or nonaromatic, comprising between 1 and 20 carbon atoms, preferably between 4 and 15 carbon atoms, preferentially between 4 and 12 carbon atoms and even more preferentially between 4 and 8 carbon atoms.

Preferably, the solvent is chosen from pentane, hexane, cyclohexane, methylcyclohexane, heptane, butane or isobutane, 1,5-cyclooctadiene, benzene, toluene, ortho-xylene, mesitylene, ethylbenzene, diethyl ether, tetrahydrofuran, 1,4-dioxane, dichloromethane, dichloroethane, tetrachloroethane, hexachloroethane, chlorobenzene, dichlorobenzene, butene, hexene and octene, pure or as a mixture.

Preferably, the solvent can be advantageously chosen from the products of the oligomerization reaction. Preferably, the solvent used is cyclohexane.

Preferably, the linear α-olefins obtained comprise from 4 to 20 carbon atoms, preferably from 4 to 18 carbon atoms, preferably from 4 to 10 carbon atoms and preferably from 4 to 8 carbon atoms. Preferably, the olefins are linear α-olefins chosen from 1-butene, 1-hexene or 1-octene.

Advantageously, the oligomerization process is carried out at a pressure between 0.1 and 10.0 MPa, preferably between 0.2 and 9.0 MPa and preferentially between 0.3 and 8.0 MPa, at a temperature of between 30 and 200° C., preferably between 35 and 150° C. and in a preferred way between 45 and 140° C.

The device which makes possible the implementation of the process according to the invention advantageously consists of a sequence of 2 to 10 gas/liquid reactors, preferably of a sequence of 2 to 8 reactors, preferably of a sequence of 2 to 6 reactors, preferably of a sequence of 3 to 6 reactors and preferably of a sequence of 2, 3, 4 or 5 reactors. The number of these reactors which are fed with gaseous ethylene preferably represents between 25% and 100% of the total number of reactors in the sequence, very preferably between 50% and 100%.

The content by weight of solvent introduced into the sequence of reactors used in the process according to the invention is between 0.5 and 10.0, preferably between 1.0 and 5.0, and with preference between 2.0 and 4.0. Advantageously, said content by weight of solvent makes it possible to obtain high levels of productivity. The content by weight of solvent is the ratio by weight of the total flow rate of injected solvent to the total flow rate of injected gaseous ethylene in the process.

The flow rate of the liquid recirculation loop of each reactor is advantageously between 500/N and 10 000/N t/h, and preferably between 800/N and 7000/N t/h, wherein N is the number of reactors in series used in the sequence.

The concentration of metal precursor of the catalytic system is preferably between 0.1 and 50.0 ppm by weight of atomic metal relative to the reaction mass, preferably between 0.4 and 30.0 ppm, preferably between 0.6 and 20.0 ppm, preferably between 0.8 and 10.0 ppm and preferably between 1.0 and 6.0 ppm by weight of atomic metal relative to the reaction mass.

According to one embodiment, the catalytic oligomerization reaction is carried out continuously.

In the case of the reactors of the sequence comprising a step of introducing ethylene, the catalytic solution, composed as described above, is injected at the same time as the ethylene into the stirred reactor(s) by conventional mechanical means known to those skilled in the art or by an external recirculation, and kept at the desired temperature. It is also possible to inject the components of the catalyst separately into the reaction medium. The ethylene is introduced via an intake valve under the control of the pressure, which keeps the latter constant in the reactor. The reaction mixture is withdrawn by means of a valve controlled by the liquid level in the reaction chamber, so as to keep said level constant. Except for the first reactor of the sequence, which is not fed with the reaction liquid fraction, the reaction liquid originating from the previous reactor in the sequence is introduced directly into the reaction chamber in the bottom or top part, with the possibility of using an element for dispersing the liquid phase, or is injected into the recirculation loop.

In the case of the reactors of the sequence not comprising injection of fresh ethylene, the system is identical except for the absence of injected ethylene.

At the outlet of the final reactor of the sequence, the catalyst is advantageously destroyed continuously by any usual means known to those skilled in the art, and then the products resulting from the reaction, and also the solvent, are separated, advantageously in a separation section downstream of the final reactor of the sequence, for example by distillation. The ethylene which has not been converted and which is recovered in the optional separation section is preferably recycled to the sequence of reactors. The catalytic system residues included in a heavy fraction at the outcome of the optional separation section can be incinerated.

Step a) of Introducing the Catalytic System

The process according to the invention comprises a step a) of introducing a catalytic system comprising a metal catalyst and an activating agent and optionally an additive and optionally of introducing a solvent or a mixture of solvents, into at least the first reactor of the sequence and, optionally, into the subsequent reactor(s) of the sequence.

Preferably, the catalytic system can be introduced into the liquid phase contained in the reaction chamber, preferably in the bottom of the reaction chamber, and/or into a portion of a liquid fraction cooled prior to the introduction of said fraction into the reaction chamber, preferably introduced in step f).

In a preferred embodiment, the catalytic system, optionally in the presence of a solvent or a mixture of solvents, is introduced solely into the first reactor of the sequence.

In another preferred embodiment, the catalytic system, optionally in the presence of a solvent or a mixture of solvents, is introduced into all of the reactors of the sequence.

Preferably, the pressure for introduction of the catalytic system into the reaction chamber is between 0.1 and 10.0 MPa, preferably between 0.2 and 9.0 MPa and preferentially between 0.3 and 8.0 MPa.

Preferably, the temperature for introduction of the catalytic system into the reaction chamber is between 30 and 200° C., preferably between 35 and 150° C. and in a preferred way between 45 and 140° C.

Step b) Introducing the Gaseous Ethylene

The process according to the invention comprises a step b) of introducing gaseous ethylene into the lower zone of the reaction chamber of at least the first reactor of the sequence. Said gaseous ethylene is introduced into the liquid phase at the lower zone of the reaction chamber, preferably on the lateral lower part of the reaction chamber, in at least the first reactor of the sequence. All of the reactors or a part of the reactors may be fed with gaseous ethylene, the first reactor always being fed with gaseous ethylene. In one preferred embodiment, the gaseous ethylene is not introduced into the final reactor of the sequence.

The number of reactors which are fed with gaseous ethylene represents between 25% and 100% of the total number of reactors in the sequence, preferably between 50% and 100%.

The gaseous ethylene introduced comprises fresh gaseous ethylene, and preferably said fresh gaseous ethylene can be combined with gaseous ethylene recycled from a downstream separation step subsequent to the oligomerization process.

During the implementation of the process according to the invention, following the step of introducing the gaseous ethylene, the liquid phase comprises undissolved gaseous ethylene; thus, according to the zones of the reaction chamber, the liquid phase corresponds to a gas/liquid mixture between notably the liquid phase and the gaseous ethylene. Preferably, the zone in the bottom of the reaction chamber below the level at which the gaseous ethylene is introduced comprises, preferably is constituted of, the liquid phase without gaseous ethylene.

Preferably, the gaseous ethylene is distributed by dispersion during its introduction into the lower liquid phase of the reaction chamber by a means capable of carrying out said dispersion uniformly over the entire section of the reactor. Preferably, the dispersion means is chosen from a distributor network with a homogeneous distribution of the ethylene injection points over the entire section of the reactor.

Preferably, the velocity of the gaseous ethylene at the outlet of the orifices is between 1.0 and 30.0 m/s. Its superficial velocity (volumetric gas velocity divided by the section of the reaction chamber) is between 0.5 and 10.0 cm/s and preferably between 1.0 and 8.0 cm/s.

Preferably, the gaseous ethylene is introduced at a flow rate between 1 and 250 t/h, preferably between 3 and 200 t/h, preferably between 5 and 150 t/h and preferably between 10 and 100 t/h.

Preferably, the flow rate of gaseous ethylene introduced in step b) is controlled by the pressure in the reaction chamber.

According to a specific implementation of the invention, a stream of gaseous hydrogen can also be introduced into the reaction chamber, with a flow rate representing 0.2% to 5.0% by weight of the flow rate of incoming ethylene, preferably representing between 0.2 and 4.0%, preferably between 0.3 and 3.0% and very preferably between 0.4 and 2.0%. Preferably, the stream of gaseous hydrogen is introduced by the pipe employed for the introduction of the gaseous ethylene.

Step c) of Withdrawing a Fraction of the Liquid Phase

The process according to the invention comprises a step c) of withdrawing a fraction of the liquid phase preferably in the lower part of the lower zone of the reaction chamber of each reactor used.

The withdrawal implemented in step c) is preferably carried out in the lower part of the lower zone of the reaction chamber in question, preferably below the level of injection of gaseous ethylene, and preferably in the bottom of the chamber. The withdrawal is carried out by any means capable of carrying out the withdrawal and preferably by a pump.

Preferably, the withdrawal flow rate is between 500/N and 10 000/N t/h, and preferably between 800/N and 7000/N t/h, wherein N denotes the number of reactors used in the sequence.

The liquid fraction withdrawn from the liquid phase is divided into two streams: a first stream and a second stream. The first stream, termed main liquid fraction, is sent to the cooling step e). For all the reactors of the sequence, apart from the final reactor, the second stream is sent to step d) of introduction into the reactor located directly downstream in the sequence. In the case of the final reactor of the sequence, the second stream corresponds to the effluent obtained at the end of the oligomerization process and may be advantageously sent to a separation section located downstream of the device, in particular of the final reactor of the sequence, used in the process according to the invention.

In another embodiment, the first and second streams can be withdrawn from the liquid phase at two distinct points of the reaction chamber, advantageously in the lower zone.

Regardless of the reactor in question in the sequence, the flow rate of said second stream is advantageously adjusted so as to keep a constant liquid level in said reactor. The flow rate of said second stream is advantageously lower than the flow rate of said first stream.

Preferably, the flow rate of said second stream is 5 to 200 times lower than the liquid flow rate of the main stream sent to the cooling step. Very preferably, the flow rate of said second stream is 5 to 150 times lower, preferably 10 to 120 times lower and with preference 20 to 100 times lower.

Step d) of Introducing the Liquid Fraction Originating from the Previous Reactor in the Sequence The process according to the invention comprises a step d) of introducing, into the reaction chamber of the downstream reactor in the sequence, the second stream corresponding to the second portion of the liquid fraction withdrawn from the upstream reactor in the sequence. This introduction is carried out by any means known to those skilled in the art, directly into the reaction chamber in one embodiment or into the recirculation loop used for the cooling step e) in another embodiment.

In the first embodiment, advantageously, in order to ensure uniform mixing of the injected liquid with the liquid present in the reaction chamber, the introduction of the liquid fraction originating from the upstream reactor in the sequence, in other words the introduction of the second stream, is carried out with a means for dispersing the injected liquid in the liquid phase present in the reaction chamber.

In the second embodiment, advantageously, a dispersion element is used to ensure the mixing of the liquid injected into the recirculation loop, by any means known to those skilled in the art.

Step e) of Cooling the Liquid Fraction

The process according to the invention comprises a step e) of cooling the main stream corresponding to a portion of the liquid fraction withdrawn in step c), for each reactor of the sequence.

Preferably, for each reactor of the sequence, the cooling step is carried out by the circulation of the main liquid stream withdrawn in step c) through one or more heat exchangers located inside or outside the reaction chamber and preferably outside.

The heat exchanger makes it possible to reduce the temperature of the liquid fraction, advantageously withdrawn and preferably of the main stream, by 1.0 to 30.0° C., preferably between 2.0 and 20° C., preferably between 2.0 and 15.0° C., preferably between 2.5 and 10.0° C., preferably by 3.0 to 9.0° C., preferably by 4.0 to 8.0° C. Advantageously, the cooling of the liquid fraction, advantageously withdrawn and preferably of the main stream, makes it possible to keep the temperature of the reaction medium within the desired temperature ranges.

Advantageously, the implementation of the step of cooling the liquid via the recirculation loop also makes it possible to carry out the stirring of the reaction medium and thus to homogenize the concentrations of the reactive entities throughout the liquid volume of the reaction chamber.

Step f) of Introducing the Cooled Liquid Fraction

The process according to the invention comprises a step f) of introducing the liquid fraction cooled in step e) for each reactor of the sequence.

For each reactor of the sequence, the introduction of the cooled liquid fraction originating from step e) is preferably carried out in the liquid phase of the reaction chamber, preferably in the upper part of the lower zone of said chamber, by any means known to those skilled in the art.

Preferably, the flow rate of introduction of the cooled liquid fraction is between 500/N and 10 000/N t/h, and preferably between 800/N and 7000/N t/h, wherein N denotes the number of reactors used in the sequence.

The effluent of the oligomerization process corresponds to the liquid portion withdrawn from the final reactor of the sequence, which is not sent to the heat exchanger, that is to say the second stream originating from the final reactor. At the outlet of the final reactor of the sequence, the products resulting from the reaction and also the solvent optionally contained in the effluent may subsequently be separated, for example by distillation.

Step g) of Recycling a Gaseous Fraction Withdrawn from the Gas Phase

The process according to the invention comprises a step g) of recycling, into at least the first reactor of the sequence, a gas fraction withdrawn from the gas phase of the reaction chamber and introduced at the lower part of the lower zone of the chamber, preferably on the lateral lower part of the reaction chamber, preferably at the bottom of the reaction chamber. The lower part denotes the lower quarter of the reaction chamber.

In one embodiment, the recycling step g) is carried out solely in the first reactor of the sequence.

In another embodiment, the recycling step g) is carried out in all the reactors of the sequence.

In another embodiment, the recycle step g) is carried out in all the reactors of the sequence, with the exception of the final reactor.

Step g) of recycling the gas fraction is also called a recycle loop. The withdrawal of the gaseous fraction implemented in step g) is carried out by any means capable of carrying out the withdrawal and preferably by a compressor.

One advantage of the recycling step according to the invention is to compensate for the phenomenon of breakthrough of ethylene into the gas headspace. The breakthrough phenomenon corresponds to the gaseous ethylene which crosses the liquid phase without dissolving and which passes into the gas headspace. When the flow rate of injected gaseous ethylene and the headspace volume are fixed at a given value, the breakthrough then leads to an increase in pressure in the reaction chamber. In a gas/liquid reactor used in the sequence, the flow rate for introduction of the ethylene in step b) is controlled by the pressure in the reaction chamber. Accordingly, in the case of an increase in the pressure in the reactor owing to a high degree of breakthrough of the ethylene into the gas phase, the flow rate of gaseous ethylene introduced in step b) decreases, thereby giving rise to a decrease in the amount of ethylene dissolved in the liquid phase and hence in the saturation. The decrease in the saturation is detrimental to the conversion of the ethylene and is accompanied by a decrease in the productivity of the reactor. The step of recycling a gas fraction according to the invention thus makes it possible to optimize the saturation of the dissolved ethylene in one or more reactors of the sequence, thereby making it possible to improve the volumetric productivity of the process.

The gas phase withdrawn in step g) may be introduced into the reaction chamber alone or as a mixture with the gaseous ethylene introduced in step b). Preferably, the gas phase is introduced as a mixture with the gaseous ethylene introduced in step b).

In one particular embodiment, the gaseous phase withdrawn in step g) is introduced into the reaction chamber by dispersion in the liquid phase in the lower zone of the reaction chamber, by a means capable of carrying out said dispersion uniformly over the entire cross section of the reactor. Preferably, the dispersion means is chosen from a distributor network with a homogeneous distribution of the points of injection of the gas phase withdrawn in step g) over the entire cross section of the reactor.

Preferably, the velocity of the withdrawn gaseous fraction at the outlet of the orifices is between 1.0 and 30.0 m/s. Its superficial velocity (volumetric gas velocity divided by the section of the reaction chamber) is between 0.5 and 10.0 cm/s and preferably between 1.0 and 8.0 cm/s.

Preferably, the rate of withdrawal of the gaseous fraction is between 0.1 and 100% by volume of the flow rate of gaseous ethylene introduced in step b), preferably 0.5 and 90.0%, preferably 1.0 and 80.0%, preferably between 2.0 and 70.0%, preferably between 4.0 and 60.0%, preferably between 5.0 and 50.0%, preferably between 10.0 and 40.0% and preferentially between 15.0 and 30.0%.

Advantageously, the flow rate for withdrawal of the gaseous fraction in step g) is controlled by the pressure within the reaction chamber, which makes it possible to maintain the pressure at a desired value or in a desired range of values and thus to compensate for the phenomenon of breakthrough of the gaseous ethylene into the headspace.

In one specific embodiment, the gaseous fraction withdrawn in step g) is divided into two streams: a first "main" gas stream, which is recycled directly into the reaction chamber, and a second gas stream.

In a preferred embodiment, said second gas stream corresponds to a bleeding of the gas headspace, which makes it possible to remove a part of the non-condensable gases.

Preferably, the flow rate of the second gas stream is between 0.005% and 1.00% by volume of the flow rate of ethylene introduced in step b), preferably between 0.01 and 0.50% of the flow rate of ethylene introduced in step b).

Oligomerization Reaction Device

Numerous reactors using a liquid phase and a gas phase consist of a reaction chamber containing a liquid phase in a lower zone comprising gaseous ethylene, and a gas phase in an upper zone, a loop for recirculating a liquid fraction to a heat exchanger, allowing the liquid fraction to be cooled before it is reinjected into the main chamber. The flow rate in the recirculation loop allows effective homogenization of the concentrations and the control of the temperature in the liquid phase within the reaction chamber.

The reaction device employed by the process according to the invention belongs to the field of gas/liquid reactors such as bubble columns. In particular, the reaction device according to the invention comprises a sequence in series of at least two gas/liquid reactors, each of the reactors comprising the following elements:

a reaction chamber i), of elongate shape along the vertical axis, containing
a liquid phase located in a lower zone, comprising and preferably consisting of the products of the reaction, dissolved and gaseous ethylene, a catalytic system and an optional solvent, and a gas phase, located in an upper zone above the lower zone, comprising gaseous ethylene and also uncondensable gases (ethane notably),
an optional means ii) for introducing the gaseous ethylene, preferably located in the lateral lower part of said reaction chamber, and preferably using a means for distributing the gaseous ethylene within said liquid phase of the reaction chamber,
an optional means iii) for introducing the catalytic system, comprising a metal catalyst, at least one activating agent and at least one additive,
a recirculation loop iv) comprising a withdrawing means at the base (preferably at the bottom) of the reaction chamber for withdrawing a liquid fraction toward a heat exchanger enabling the cooling of said liquid, and a means for introducing said cooled liquid, said introduction being carried out into the liquid phase in the upper part of the lower zone of the reaction chamber,
a recycle loop v) for the gas phase into the lower zone of the liquid phase, comprising a means for withdrawing a gaseous fraction at the gas phase of the reaction chamber and a means for introducing said withdrawn gaseous fraction into the liquid phase in the lower zone of the reaction chamber, each reactor of the sequence, except for the first, being fed by a second part of the liquid fraction withdrawn from the reactor upstream in the sequence, by feed means vi), which may be a pipe directly feeding the reaction chamber in one embodiment, or a pipe joining the recirculation loop used for the cooling step e) in another embodiment, at least the first reactor of the sequence always being fed with catalytic system and with gaseous ethylene and optionally with solvent.

i) A Reaction Chamber

According to the invention, any reaction chamber known to those skilled in the art and capable of carrying out the process according to the invention can be envisaged. Preferably, the reaction chamber is cylindrical in shape and has a height to width ratio (denoted H/W) of between 1 and 17, preferably between 1 and 8, preferably between 2 and 7, and preferentially between 2 and 4.

Preferably, the reaction chamber comprises a means for purging the uncondensable gases in the gas phase.

Preferably, the reaction chamber also comprises a pressure sensor, allowing the pressure within the reaction chamber to be controlled and, preferably, to be kept constant. Preferably, in the event of a decrease in the pressure, said pressure is kept constant by the introduction of gaseous ethylene into the reaction chamber.

According to the invention, in the event of the phenomenon of breakthrough of ethylene into the gas phase, said pressure is kept constant by the implementation of the recycle loop v), described below.

Accordingly, the gas headspace recycle loop makes it possible, advantageously, in the event of ethylene breakthrough, to keep the saturation of ethylene dissolved in the liquid phase of the lower zone at a given value.

Preferably, the reaction chamber also comprises a liquid level sensor; said level is kept constant by adjusting the flow rate of the effluent withdrawn in step c). Preferably, the level sensor is located at the interphase between the liquid phase and the gas headspace.

ii) A Means for Introducing Ethylene

According to the invention, for the reactor(s) fed with gaseous ethylene of the sequence, the reaction chamber i) comprises a means for introducing the gaseous ethylene located in the lower part of said chamber, more particularly in the lateral lower part.

In one particular embodiment, the final reactor of the sequence does not comprise a means for introducing the gaseous ethylene.

Preferably, the means ii) for introducing the ethylene is chosen from a pipe, a network of pipes, a multitubular distributor, a perforated plate or any other means known to those skilled in the art.

In one specific embodiment, the means for introducing the ethylene is located in the recirculation loop iv).

Preferably, a gas distributor, which is a device which makes it possible to disperse the gas phase uniformly over the entire liquid cross section, is positioned at the end of the introduction means ii) within the reaction chamber i). Said device comprises a network of perforated pipes, the diameter of the orifices of which is between 1.0 and 12.0 mm, preferably between 3.0 and 10.0 mm, in order to form ethylene bubbles of millimetric size in the liquid.

iii) A Means for Introducing the Catalytic System

According to the invention, the first reactor of the sequence comprises a means iii) for introducing the catalytic system. Optionally, the reactors of the sequence other than the first reactor may comprise said means.

Advantageously, the means for introducing the catalytic system can be any means such as a pipe, capable of introducing a liquid fraction that may contain the catalytic system into the reaction chamber i).

Preferably, the introduction means iii) is located on the lower part of the reaction chamber and preferably at the bottom of said chamber.

According to an alternative embodiment, the catalytic system is introduced into the recirculation loop iv).

The means iii) for introducing the catalytic system is chosen from any means known to those skilled in the art and is preferably a pipe.

In the embodiment wherein the catalytic system is employed in the presence of a solvent or of a mixture of solvents, said solvent is introduced by an introduction means located in the lower part of the reaction chamber, preferably at the bottom of the reaction chamber or else in the recirculation loop.

iv) A Recirculation Loop

According to the invention, the liquid phase is rendered homogeneous and also the temperature within the reaction chamber is regulated by the use of a recirculation loop comprising a means on the lower part of the reaction chamber, preferably at the bottom, for withdrawing a liquid fraction toward one or more heat exchanger(s), thereby enabling the cooling of said liquid, and a means for introducing said cooled liquid into the upper part of the reaction chamber.

The recirculation loop can advantageously be implemented by any necessary means known to those skilled in the art, such as a pump for the withdrawal of the liquid fraction, a means capable of regulating the flow rate of the withdrawn liquid fraction, or else a pipe for bleeding off at least a portion of the liquid fraction.

Preferably, the means for withdrawing the liquid fraction from the reaction chamber is a pipe.

The heat exchanger(s) capable of cooling the liquid fraction is (are) chosen from any means known to those skilled in the art.

The recirculation loop enables effective homogenization of the concentrations and makes it possible to control the temperature in the liquid phase within the reaction chamber.

v) A Gas Headspace Recycle Loop

According to the invention, the device comprises a loop for recycling the gas phase into the lower part of the liquid phase. Said loop comprises a means for withdrawing a gaseous fraction in the gas phase of the reaction chamber, that is to say in the upper zone of said reaction chamber, and a means for introducing said withdrawn gaseous fraction into the liquid phase in the lower part of the reaction chamber.

The recycle loop makes it possible, advantageously, to compensate for the phenomenon of breakthrough and to prevent the pressure in the reaction chamber from increasing, while keeping the saturation of ethylene dissolved in the liquid phase at a desired level.

Another advantage of the recycle loop is to improve the volume productivity of the device and thus to reduce the costs. In one preferred embodiment, the recycle loop additionally comprises a compressor.

In one embodiment, the withdrawn gaseous fraction is introduced via the means ii) for introducing the gaseous ethylene.

In another embodiment, the gaseous fraction withdrawn is introduced via a gas distributor, which is a device which makes it possible to disperse the gas phase uniformly over the entire liquid cross section and is positioned at the end of the introduction means within the reaction chamber i). Said device comprises a network of perforated pipes, the diameter of the orifices of which is between 1.0 and 12.0 mm, preferably between 3.0 and 10.0 mm, in order to form ethylene bubbles of millimetric size in the liquid.

Preferably, the means for introducing the withdrawn gaseous fraction is chosen from a pipe, a network of pipes, a multitubular distributor, a perforated plate or any other means known to those skilled in the art.

vi) Liquid Feed Means

For each reactor of the sequence used in the process according to the invention, with the exception of the first reactor of the sequence, liquid feed means allow the introduction of the second portion of the liquid fraction withdrawn from the reactor upstream in the sequence. These feed means vi) may be a pipe directly feeding the reaction chamber in one embodiment, or a pipe joining the recirculation loop used for the cooling step e) in another embodiment.

The device according to the invention preferably consists of a sequence of 2 to 10 gas/liquid reactors, preferably a sequence of 2 to 8 reactors, preferably a sequence of 3 to 8 reactors, preferably a sequence of 2 to 6 reactors, preferably a sequence of 3 to 6 reactors, preferably 2, 3, 4 or 5 reactors. The number of these reactors which are fed with gaseous ethylene represents between 25% and 100% of the total number of reactors in the sequence, preferably between 50% and 100%.

One advantage of the present invention is thus that of making it possible to achieve selectivities for olefins which are superior to those achieved with a device according to the prior art comprising only a single gas/liquid reactor, while retaining a high level of conversion of the gaseous ethylene into linear olefins and preferably into linear alpha-olefins.

BRIEF DESCRIPTION OF THE DRAWINGS

FIG. 2 provides a schematic illustration of one particular embodiment of the subject matter of the present invention, without limiting the scope thereof.

EXAMPLES

Figure 1:
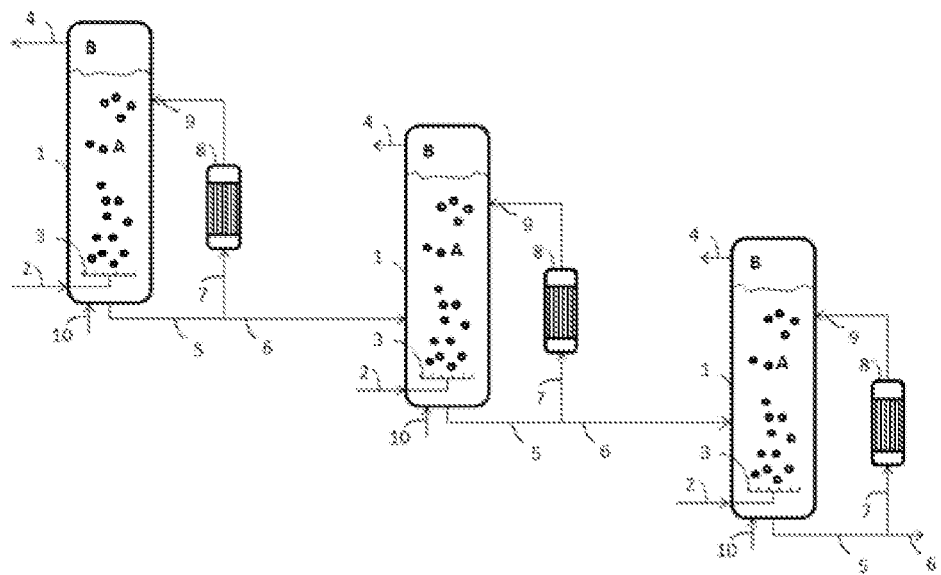
FIG. 1 illustrates a reaction device according to the prior art. This device comprises a sequence of three gas-liquid reactors; each of the reactors consists of a reaction chamber (1) comprising a lower zone comprising a liquid phase A and an upper zone comprising a gas phase B, of a means (2) for introducing the gaseous ethylene via a gas distributor (3) into the liquid phase A. The gas phase B comprises a purging means (4). A pipe for withdrawing a liquid fraction (5) is located in the bottom of the reaction chamber (1) of each of the three reactors. Said fraction (5) is divided into two streams, a first, main stream (7) which is sent to a heat exchanger (8) and then introduced via a pipe (9) into the liquid phase A, and a second stream (6), which corresponds to the effluent sent to a later step. The pipe (10) in the bottom of the reaction chamber of each of the three reactors makes possible the introduction of the catalytic system.
Figure 2:
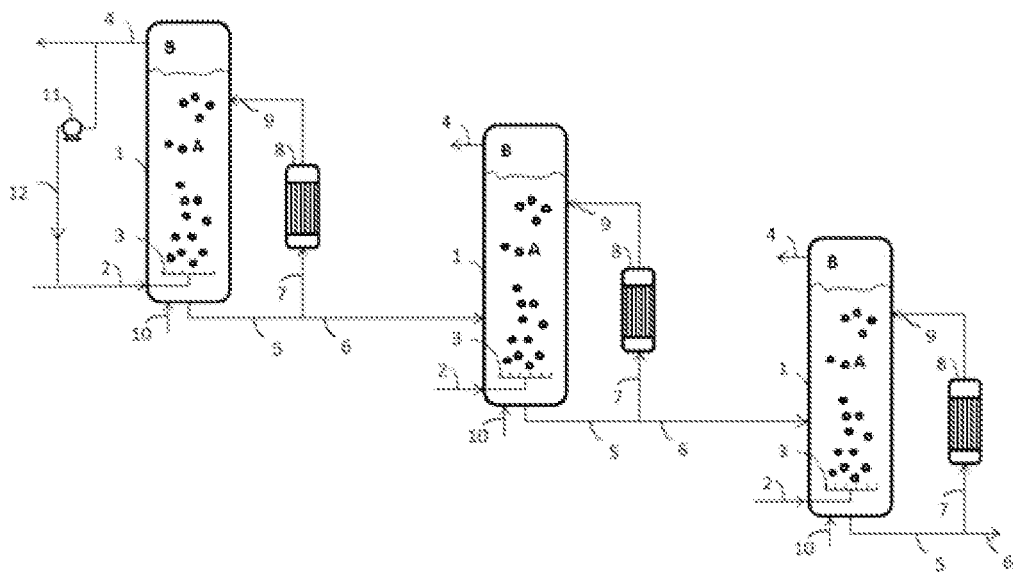
FIG. 2 illustrates a device which makes possible the implementation of the process according to the invention. Said device differs from the device of FIG. 1 in that, in the first reactor of the sequence, a gaseous fraction of the gas phase B is sent to a compressor (II) and is recycled, via a pipe (12) connected to the means (2) for introducing gaseous ethylene, into the lower part of the zone A comprising the liquid phase A.

The examples below illustrate the invention without limiting the scope thereof.

Example 1: Comparative Example Corresponding to a Sequence of Four Reactors without Gas Headspace Recycle Example 1 uses a sequence in series of 4 gas-liquid reactors for the oligomerization of ethylene.

The catalytic system introduced into the reaction chamber of all the reactors of the sequence is a catalytic system based on chromium, as described in patent FR 3 019 064, in the presence of a solvent which is cyclohexane, in such a way as to ensure a chromium content of 5 ppm by weight in each reactor of the sequence.

The reaction volume of each reactor is 45.7 m$^3$. The 4 reactors of the sequence are all operated at a temperature of 135° C. and a pressure of 5.3 MPa of ethylene.

The overall residence time in the reactor sequence is 17.5 min.

The performance levels of this reaction device make it possible to convert 50.80% of the injected ethylene for a content by weight of solvent of 3.7, and to achieve a level of 1-hexene selectivity of 90.9%.

The sequence of four reactors without gas headspace recycle has a volumetric productivity of 177 kg of 1-hexene produced per hour and per m$^3$ of reaction volume.

Example 2: According to the Invention Using a Sequence in Series of 4 Reactors with Gas Recycle Example 2 according to the invention uses a sequence in series of 4 gas-liquid reactors for the oligomerization of ethylene, each of the 4 reactors being fed with ethylene, and comprising the step of recycling the gas fraction.

The catalytic system is introduced into the reaction chamber of all the reactors of the sequence. Said system is a catalytic system based on chromium, as described in patent FR 3 019 064, in the presence of cyclohexane. As in the previous example, the 4 reactors of the sequence are all operated at a temperature of 135° C. and a pressure of 5.3 MPa.

The overall residence time in the reactor sequence is 12.3 min.

The 4 reactors in series of the sequence implement a step of recycling the gas fraction representing 9.0% of the flow rate of fresh ethylene feeding each of said reactors.

The use of the recycle loop according to the invention makes it possible, for one and the same performance level compared to the sequence of example 1 (conversion of 50.80% of the injected ethylene and alpha-olefin selectivity of 90.9%, for a solvent content by weight of 3.7), in a reaction volume of 32.2 m$^3$ for each reactor, with a catalytic concentration of 7.1 ppm by weight of chromium, to increase the volumetric productivity by 42% and thus to produce 251 kg of 1-hexene per hour and per m$^3$ of reaction volume.

The invention claimed is:

1. A process for the oligomerization of ethylene, carried out at a pressure of between 0.1 and 10 MPa, at a temperature of between 30 and 200° C., in a sequence of at least two gas/liquid reactors placed in series, said process comprising the following steps:

a) a step of introducing a catalytic oligomerization system comprising at least one metal precursor, optionally at least one activating agent and optionally at least one additive into at least the first reactor of the sequence comprising a reaction chamber comprising a liquid phase in a lower zone and a gas phase in an upper zone, b) a step of introducing gaseous ethylene into the lower part of the reaction chamber of at least the first reactor of the sequence, c) for each reactor, a step of withdrawing a fraction of liquid phase from the lower part of the reaction chamber of the reactor, the liquid fraction being separated into two streams: a first stream corresponding to a first portion of the liquid fraction, termed main liquid fraction, which is sent to the cooling step c); a second stream corresponding to the second portion of the liquid fraction which constitutes the liquid feed of the reactor, located downstream in the sequence, unless the liquid fraction withdrawn is from the final reactor of the sequence, and for the final reactor of the sequence, the second stream corresponds to the effluent obtained at the end of the oligomerization process, d) a step of introducing said second portion of the liquid fraction withdrawn from the reactor located upstream into the reaction chamber of the reactor located downstream in the direction of flow, e) a step of cooling said main liquid fraction withdrawn from the reactor located upstream in step c) by passing said first portion of the liquid fraction into a heat exchanger in order to obtain a cooled liquid fraction, f) a step of introducing said liquid fraction cooled in step e) at the top of the reaction chamber of said reactor, steps a) to f) being carried out for each reactor of the sequence, and g) a step of recycling a gas fraction, withdrawn from the upper zone of the reaction chamber and introduced at the lower part of said reaction chamber into the liquid phase, said recycling step g) being carried out in at least the first reactor of the sequence.

2. The process as claimed in claim 1, wherein the sequence of reactors uses from 2 to 10 gas/liquid reactors placed in series.

3. The process as claimed in claim 1, wherein the gas phase withdrawn in step g) is introduced as a mixture with the gaseous ethylene introduced in step b).

4. The process as claimed in claim 1, wherein the rate of withdrawal of the gaseous fraction in step g) is between 0.1 and 100% of the flow rate of gaseous ethylene introduced in step b).

5. The process as claimed in claim 1, wherein the gaseous fraction withdrawn in step g) is introduced at the lateral lower part of the reaction chamber.

6. The process as claimed in claim 1, wherein the rate of withdrawal of the gaseous fraction in step g) is controlled by the pressure within the reaction chamber.

7. The process as claimed in claim 1, wherein a second purge gas stream is withdrawn from the gas phase.

8. The process as claimed in claim 7, wherein the flow rate of the second gaseous stream is between 0.005 and 1.00% of the flow rate of ethylene introduced in step b).

9. The process as claimed in claim 1, using a solvent and having a content by weight of solvent introduced into the sequence of reactors of between 0.5 and 10.0.

10. The process as claimed in claim 1, wherein a gaseous hydrogen stream is introduced in step b) into the reaction chamber, with a flow rate representing 0.2 to 5.0% by weight of the flow rate of incoming ethylene.

11. The process as claimed in claim 1, wherein the concentration of metal precursor in the catalytic system is between 0.1 and 50.0 ppm by weight of atomic metal relative to the reaction mass.

12. The process as claimed in claim 1, wherein the catalytic oligomerization reaction is carried out continuously.

13. The process as claimed in claim 1, wherein the oligomerization makes it possible to obtain linear olefins comprising from 4 to 20 carbon atoms.

14. A reaction device for implementing the process as claimed in claim 1, wherein each of the reactors comprises the following elements:

a reaction chamber i), of elongate shape along the vertical axis, a lower zone and an upper zone above the lower zone, an optional means ii) for introducing gaseous ethylene into said reaction chamber, the first reactor of the sequence always comprising said means ii) for introducing the gaseous ethylene, an optional means iii) for introducing the catalytic system, the first reactor of the sequence always comprising said means iii) for introducing the catalytic system, a recirculation loop iv) comprising a withdrawing means at the base of the reaction chamber for withdrawing a liquid fraction and a heat exchanger, and a means for introducing said cooled liquid into the upper part of the lower zone of the reaction chamber, a gas phase recycle loop v), comprising a means for withdrawing a gas fraction at the level of the upper zone of the reaction chamber, and a means for introducing said withdrawn gas fraction into the lower zone of the reaction chamber, with the exception of the first reactor, at least one means vi) for feeding a second portion of the liquid fraction withdrawn from the upstream reactor in the sequence, at least the first reactor of the sequence always being fed with catalytic system and with gaseous ethylene.

15. The device as claimed in claim 14, wherein the means for introducing the withdrawn gas fraction into the recycle loop corresponds to the means ii) for introducing the gaseous ethylene.

16. The device as claimed in claim 14, wherein said one or more feed means is a pipe directly feeding the reaction chamber.

17. The device as claimed in claim 14, wherein said one or more feed means is a pipe joining the recirculation loop used for the cooling step e).

* * * * *